United States Patent [19]

Russo

[11] 4,114,608
[45] Sep. 19, 1978

[54] INHALATION DEVICE

[75] Inventor: Ronald D. Russo, Hamden, Conn.

[73] Assignee: Chesebrough-Pond's Inc., Greenwich, Conn.

[21] Appl. No.: 753,840

[22] Filed: Dec. 23, 1976

Related U.S. Application Data

[63] Continuation-in-part of Ser. No. 657,241, Feb. 11, 1976, Pat. No. 4,086,918.

[51] Int. Cl.$^2$ ............................................. A61B 5/08
[52] U.S. Cl. ................................... 128/2.08; 272/99
[58] Field of Search ............ 128/2.08, 2.05 V, 142 R, 128/185, 202, 205, 145.8, 147, 201, 208; 272/99 R; 73/419, 209; 116/117 B, 117 C, 117 R

[56] References Cited

U.S. PATENT DOCUMENTS

| 393,869 | 12/1888 | Warren | 128/201 |
|---|---|---|---|
| 515,637 | 2/1894 | Wilhide | 272/99 R |
| 714,141 | 11/1902 | Cady | 128/2.08 |
| 793,177 | 6/1905 | Cady | 128/2.08 |
| 892,432 | 7/1908 | Judson | 272/27 |
| 1,926,748 | 9/1933 | MacKenzie et al. | 128/2.05 R |
| 2,100,898 | 11/1937 | Bernett | 273/95 |
| 3,087,278 | 4/1963 | Waggle, Jr. | 46/44 |
| 3,633,421 | 1/1972 | Phillips | 73/209 |
| 3,635,214 | 1/1972 | Rand et al. | 128/2.08 |
| 3,695,608 | 10/1972 | Hanson | 128/2.08 |
| 3,754,546 | 8/1973 | Cooper | 272/99 R |
| 3,898,987 | 8/1975 | Elam | 128/145.8 |
| 4,025,070 | 5/1977 | McGill et al. | 272/99 R |
| 4,037,836 | 7/1977 | Puderbaugh et al. | 272/99 R |

FOREIGN PATENT DOCUMENTS 8,662 of 1903 United Kingdom ................. 272/99 R

*Primary Examiner*—Henry J. Recla
*Attorney, Agent, or Firm*—Morgan, Finnegan, Pine, Foley & Lee

[57] ABSTRACT

An inhalation device which induces respiratory exercise and which is inexpensive, safe and easy to handle and operate. The device includes a flow measurement container having a chamber in which is housed a flow rate indicator, such as a light-weight article or ball that normally rests at the bottom of the chamber. Extending into the container are opposing openings, one of which connects the chamber to a passageway through which a person inhales to remove air from the chamber, and the other of which connects the chamber to atmosphere for lifting the indicator upon inhalation.

In one embodiment the opposed openings extend through the top wall of the container. A restricted opening or port connects the chamber to atmosphere and a larger opposing opening or port to the passageway.

In another embodiment the openings are provided in the upper and lower portions of the container. The upper opening connects the top portion of the chamber to the passageway and the lower opening connects the lower portion of the chamber to atmosphere for lifting the indicator.

With the inhalation device of the invention, the user nurse, or therapist can readily measure the amount inspired. A predetermined amount of inhalation for a given time (precalibrated rate of flow) is required to raise the indicator to the top of the chamber, and predetermined additional amounts of inhalation for given additional times are required to maintain the indicator at the top thereof.

15 Claims, 14 Drawing Figures

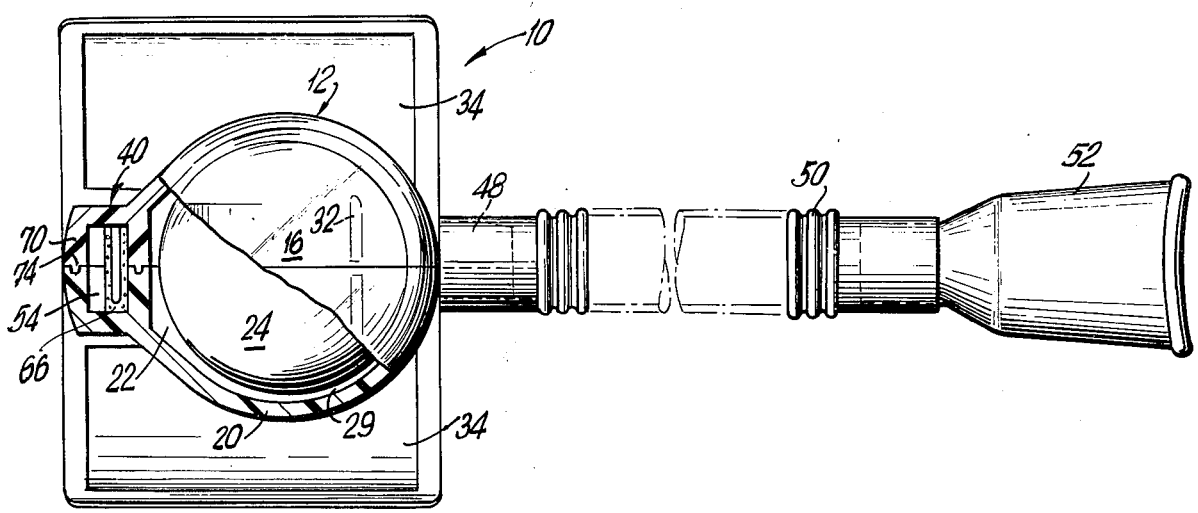
FIG.10
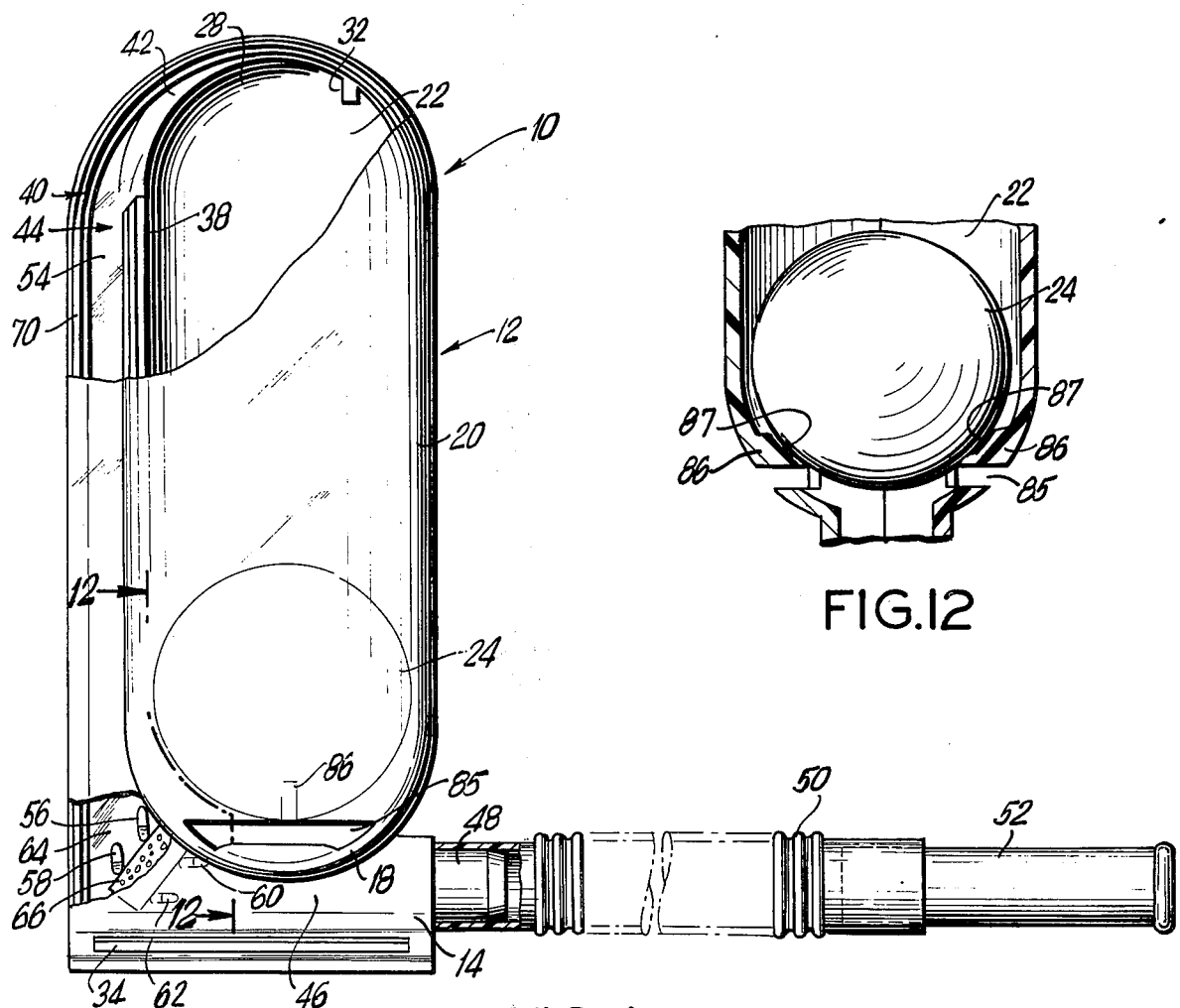
FIG.12
FIG.11

INHALATION DEVICE

This application is a continuation-in-part of my application Ser. No. 657,241, filed Feb. 11, 1976, now U.S. Pat. No. 4,086,918.

FIELD OF THE INVENTION

The present invention relates to an inhalation device for inducing a person to expand and use his or her lungs and respiratory musculature.

BACKGROUND OF THE INVENTION

It is often necessary to induce patients to expand and use their lungs and respiratory musculature. Post-surgical, bedridden, inactive, obese and geriatric patients do not utilize their respiratory systems fully. Pain, illness and feebleness inhibit use. As a consequence, these people are prone to pulmonary complications such as lung congestion, atelectasis and pneumonia. The inefficient use of the respiratory system also can retard healing and cause muscle atrophy.

Thus, a need exists to provide patients with an incentive which encourages use of their respiratory systems. In general, presently available apparatus for inducing said use by inhalation is relatively expensive and awkward to handle. Further, the apparatus is comparatively costly and complex, and is generally limited to hospital use because of the complexities and costs. In addition, presently available apparatus is made up of a multiplicity of parts which, when dropped are susceptible to breakage and which are costly to replace.

It is an object of this invnetion, therefore, to provide a new and improved device which induces respiratory exercises through inhalation without drawbacks of presently available devices and systems.

Among the other objects of this invention is to provide an inhalation device which provides the requisite incentive and encourages use by ease of handling and operation; to provide an inhalation device which is safe to use; to provide an inhalation device, the successful use of which easily can be seen and measured by the patient, nurse or others; and to provide an inhalation device which accomplishes the foregoing while being relatively inexpensive.

Additional objects and advantages will be set forth in part hereinafter and in part will be obvious herefrom or may be learned with the practice of the invention, the same being realized and obtained by means of the respiratory stimulator recited in the appended claims.

SUMMARY OF THE INVENTION

In accordance with the invention there is provided an incentive inhalation device, comprising a flow measurement container. In its upright position the container has a top wall, a bottom wall and a see-through vertical wall. Extending from the top and bottom wall within the container is a chamber in which a flow rate indicator, such as a light-weight article or ball, normally rests at the bottom thereof. A clearance fit is provided between the indicator and chamber wall which allows for free vertical movement of the indicator but restricts air flow about the indicator for causing it to rise when a precalibrated inhalation effort is achieved.

Extending into the chamber are opposing openings. One of the openings connects the upper portion of the chamber to an air inhalation passageway which is connected to an air outlet.

In one embodiment the opposing opening also extends into the upper portion of the chamber and connects the chamber to the surrounding atmosphere. In this embodiment the opposing openings or ports extend through the top wall of the container and the passageway port is the larger of the two openings.

In another embodiment the openings are provided in the upper and lower portions of the container. The upper opening connects the top portion of the air inhalation passageway to the chamber while the lower opening connects the lower portion of the chamber to atmosphere for lifting the indicator.

Preferably, the container is positioned on a base which makes the device self-supporting in the vertical position, and the inhalation passageway extends from an outlet in the front of the base, under the container and upwardly in a vertical channel to provide a clear view of the indicator to the users so that they can readily measure their efforts.

Connected to the outlet of the passageway are means, such as flexible tubing and a mouthpiece, which allow a person to withdraw air from the container chamber upon inhaling.

In use, a person places his or her mouth over the mouthpiece and inhales. This causes air to be withdrawn from the top of the chamber.

In the embodiment with opposing openings in the container top wall, the flow is across the chamber from the restricted port to the larger port and down through the passageway. As the person continues to inhale, a venturi effect created by the restricted port causes a pressure differential within the chamber with the air pressure at the top of the chamber being less than the air pressure at the bottom chamber. At the same time a lifting air stream is created by the air rushing into the chamber through the restricted port and through the clearance between the flow indicator and the chamber wall. Air flows down and about the indicator, hits the bottom wall and flows upwardly against the indicator. When a precalibrated inhalation effort is achieved within a predetermined time the pressure differential and the lifting air stream will cause the indicator to move to the top of the container and be maintained there until the person's efforts drop below the desired flow rate.

In the illustrative embodiment of the device with the opposing top ports show in the drawings and described hereinafter at least 750 cubic centimeters per second must be inspired by the user to raise and maintain the ball to the top of the container. Accordingly, to maintain the ball at the container top for two seconds, at least 1500 cubic centimeters must be inspired within that time, and to maintain the ball at the top for four seconds, at least 3000 cubic centimeters must be inspired during this interval.

In the embodiment with the upper and lower openings the inhalation of air causes atmospheric air to flow through the lower opening against the indicator, up through the chamber and into the air inhalation passageway. When the precalibrated inhalation effort is achieved within the predetermined interval the lifting air stream lifts the indicator to the top of the chamber where it is maintained for as long as the person exerts at least the precalibrated effort.

In the embodiment of the invention hereafter described and illustrated which includes upper and lower openings in the container, at least 600 cubic centimeters per second must be inspired by the user to raise and maintain the ball at the top of the container. Thus, to maintain the ball at the container top for two seconds at least 1200 cubic centimeters must be inspired within that time. It has been found, moreover, that with this embodiment of the invention the device has somewhat great flexibility because it more readily can be constructed to provide lower precalibrated rates of flow.

Additionally, by tilting the devices of the invention, e.g., rearwardly, the force needed to overcome the force of gravity in the indicator is lessened so that the indicator can be raised to the top of the container more easily. Particularly ill or feeble patients are thereby provide with an incentive level they can achieve, and, in so doing, obtain needed respiratory exercise. To be able to accurately measure the flow rate when the container is tilted, means, such as a platform, are provided which can maintain the container at the desired angle. In the embodiment hereinafter described and illustrated in the drawings, the platform is provided with means for maintaining the container at several predetermined angles. For example, when the container with the opposing ports in the top thereof is tilted rearwardly some 85°, an inhalation rate of only 250 cubic centimeters per second is required to raise and maintain the ball at the top of the container.

The devices of the invention are particularly useful for inducing and measuring sustained inspiration which meets at least a desired minimum inhalation effort.

Also, in accordance with the invention, means are provided within the chamber to prevent the indicator from actually contacting the bottom or top walls within the chamber to facilitate moving of the indicator upward and to prevent the indicator from closing the port and surprising the user through the disruption of air flow.

In construction, the device is compact and safe. Within the inhalation passageway there is provided a filter which prevents loose particles picked up in the air flow from exiting and being inhaled by the user. In addition, where the device is made of several plastic components, they are placed together and are preferably ultrasonically welded into a single integral break resistant unit. This obviates the need of deleterious materials, such as glue, which are known to give off residual vapors over a long period of time.

In addition, a dispenser, such as a nebulizer, can be placed at the outlet end of the device for inhalation of medicine upon inspiration by the patient.

BRIEF DESCRIPTION OF THE DRAWINGS

The following are detailed descriptions and illustrations of preferred embodiments of the invention. It is to be understood that the invention is capable of modification and variation apparent to those skilled in the art within the spirit and scope of the invention.

In the drawings:

FIG. 10 is a plan view of the device illustrated in FIG. 9 with the top of the container broken away to show details of construction.

FIG. 11 is a side view of the device illustrated in FIG. 9 in which the container and vertical channel are partially broken away to show details in construction.

FIG. 12 is a sectional view of FIG. 10 taken along the lines 12—12.

Figure 1:
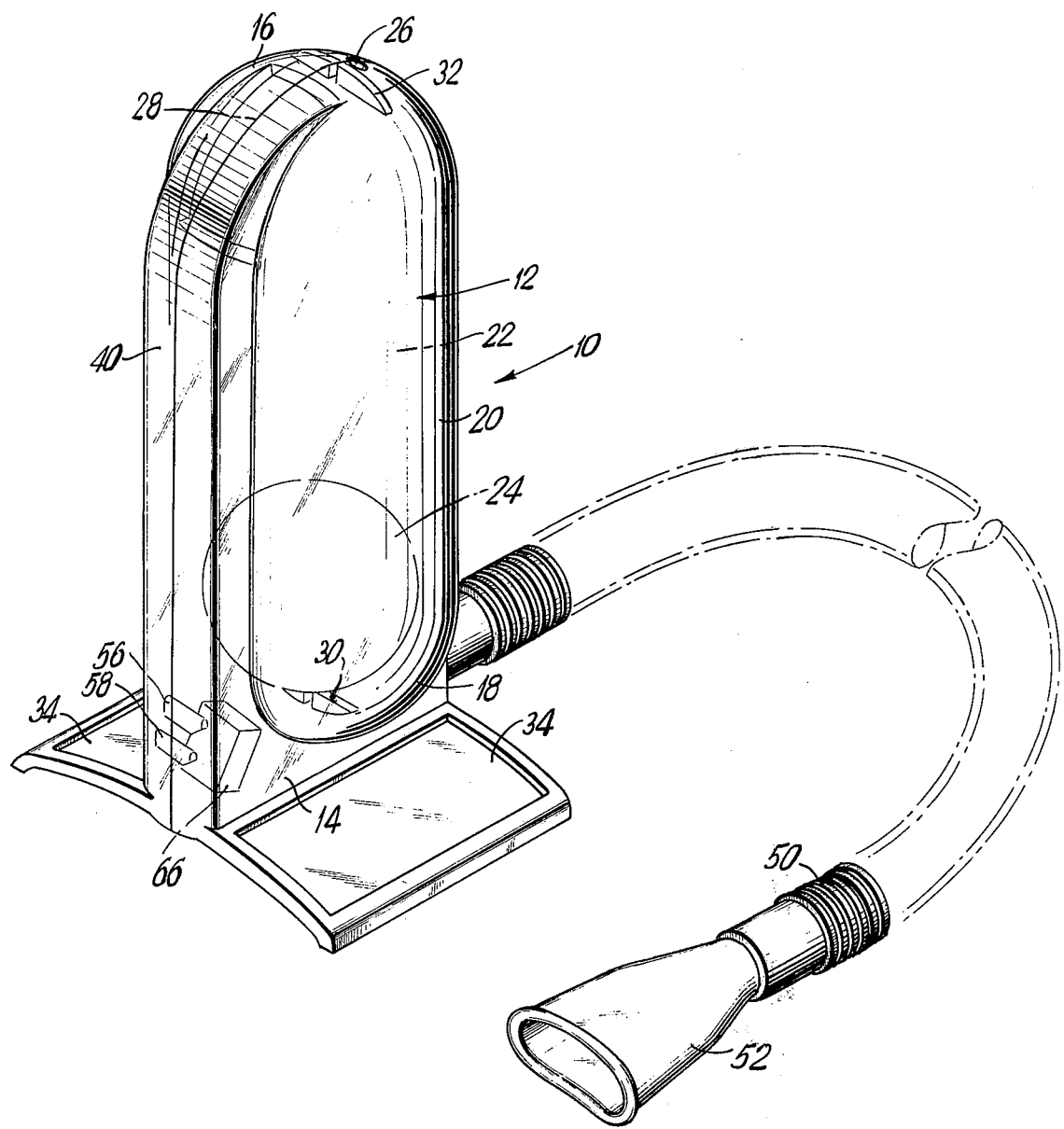
FIG. 1 is a perspective view of an inhalation device constructed in accordance with the present invention wherein opposing ports are provided in the top wall of the container.

Referring to the drawings, the inspirator 10 shown in FIGS. 1-7 is a transparent integral unit which includes a flow measurement container 12, mounted on a base 14.

The container 12 has a hemispherically or dome-shaped top 16 and bottom 18 with a cylindrically shaped intermediate wall 20 which defines a chamber 22 for a light-weight indicator 24, such as a small colored plastic ball.

Extending through the top 16 are two ports 26 and 28. The port 26 extends through the front portion of the top 16 and connects the chamber 22 with the surrounding atmosphere. The port 26 is circular in cross-section and is restricted in breadth to provide a venturi effect with the chamber 22. The port 28 extends through the back portion of the top 16 and connects the chamber 22 with air passageway hereinafter described in detail. The port 28 is rectangular in cross-section and has a breadth substantially larger than the breadth of the restricted port 26.

The relative diameter of the ball 24 to the inner diameter of the wall 29 allows free movement of the ball 24 within the chamber 22 while restricting air flow about the ball. If the gap or clearance between the ball 24 and wall 20 is too small, the ball 24 may become stuck in the chamber 22. If the gap is too large, the desired inhalation effort will not effect pressure differentials and air streams within the chamber 22 necessary to lift the ball 24. In the illustrated embodiment a total clearance fit or gap between the wall 29 and ball 24 of about 0.125 inches to 0.25 inches is provided.

Similarly, the relative sizes of the ports 26 and 28 are such that they provide the requisite incoming air stream through port 26 when the desired inhalation is achieved. In this device exhalation or blowing into the chamber 22 does not cause the ball 24 to rise at all.

Instead, the inner surfaces of the top 16 and wall 20 become clouded because of condensation. In the illustrated embodiment the port 26 has a diameter of about 0.187 inches providing an opening having an area of 0.008 square inches and the port 28 has a height of about 0.25 inches and a width of about 0.50 inches providing an opening having an area of 0.125 square inches. In other words, port 28 has an area which is about sixteen times that of port 26.

In general, upon inhalation air is removed from the top of the chamber 22 through port 28 causing atmospheric air to rush into the chamber 22 through port 26. A portion of such air will move across the top chamber 22 and into the passageway through port 28 and a portion will move downwardly around the ball 24 and be redirected upwardly against the ball 24 by the bottom 18. This flow creates a lifting air stream and a pressure differential in the chamber 22 with the air pressure at the top of the chamber being less than at the bottom, all of which causes the ball to rise. To facilitate the rise of the ball 24 and to prevent the ball 24 from closing port 26, ridges 30 and 32 are provided within the container 12. The lower ridge 30 extends upwardly and prevents the ball from contacting the bottom of the container. The upper ridge 32 depends downwardly adjacent to the port 26 to prevent closing the port 26 by the rising ball 24 which would disrupt the desired flow of air and cause surprise or shock to the user.

The base 14 on which the container bottom 18 is positioned, includes a pair of arms 34 which extend laterally from the two sides of the base 14 outwardly and downwardly to serve as a stand for the inspirator so that it will stand by itself in an upright or vertical position.

Extending vertically upwardly from the base 14 and continuous with the container rear wall 38 is a vertical shaped channel 40 which terminates at its upper end in a tapered segment 42 that is inwardly curved to compliment the dome shaped top 16.

Extending through the base 14 and channel 40 and container rear wall 38 is an "L" shaped air passageway 44. The horizontal section 46 of the passageway 44 is centrally positioned and extends directly under the container bottom 18, and terminates at its outer or front end in an outwardly extending integral tube 48. Slidably fitted over the outlet tube 48 is a flexible accordian tubing 50 which has at its other end a mouthpiece 52 slidably fitted thereinto.

The vertical section 54 of the passageway 44 extends from the inner or back end of the horizontal section 46 vertically upward to the port 28. At the juncture of the vertical and horizontal sections of the passageway 44 there is provided two vertically spaced and two horizontally spaced tabs 56, 58, 60 and 62, respectively. The inner vertical tab 56 is placed above vertical tab 58 and inner horizontal tab 60 is placed in front of tab 62 to define a slot 64 which is at an acute angle with the horizontal section 46 of the passageway 44. Extending across the passageway 44 and force fitted within the angular slot 64 is a rectangularly shaped filter 66 which captures loose particles that may pass through port 26 and into a passageway 44.

In operation, the patient or user places his or her mouth over the mouthpiece 52 and inhales. This action causes air to be withdrawn from the top of the container 12 and creates a pressure differential in the chamber 22, wherein the pressure in the lower portion of the chamber 22 is higher than the pressure in the upper part of the chamber 22. At the same time, inrushing air flows downwardly about the ball 24 and is reflected upwardly by the bottom 18 against the ball 24. When the pressure differential and lifting air stream reach a predetermined level that corresponds to the desired inhalation rate, the ball 24 within the chamber 22 will begin to rise. Continued inhalation at the predetermined rate will cause the ball 24 to rise to the top of the chamber 22 and contact ridge 32 where it will remain as long as the user continues to withdraw sufficient air from the top of the chamber 22 at that rate.

The device of the present invention therefore measures the minimum flow rate of inspiration needed to lift and maintain ball 24 of the container top 16. In the device illustrated in the drawings, the ball 24 is about 1.50 inches in diameter and weighs 2.5 grams. The ball 24 will move to the top of the chamber 22, which is about 5.5 inches in length and 1.75 inches in cross section, when the inhalation flow rate from the chamber 22 is at least about 750 cubic centimeters per second. To thereafter maintain the ball 24 in the suspended state, a flow rate of at least about 750 cubic centimeters must be maintained. From this flow rate total volume inspired is easily calculated, e.g., at least 1500 cubic centimeters for two seconds; at least 3000 cubic centimeters for four seconds; at least 4500 cubic centimeters for six seconds. Thus, a patient, nurse, and others can tell that at least so many cubic centimeters have been inspired by timing how long the ball 24 remains suspended.

Moreover, the flow rate of 750 cubic centimeters per second for the device 10 illustrated in the drawings corresponds to the mid-range of a deep breath. It is within the scope of this invention to provide devices 10 with different flow rates which can be made to correspond to the condition of the patient. For example, by further restricting the port 26 a flow rate which corresponds to a full deep breath, e.g., 1000 cubic centimeters per second, is provided. This device can be used for a patient who is near full recovery. Correspondingly, by enlarging the port 26 a flow rate which corresponds to lower range of a deep breath, e.g., 500 cubic centimeters per second, is provided. This device can be used for a feeble or seriously ill patient.

Figure 7:
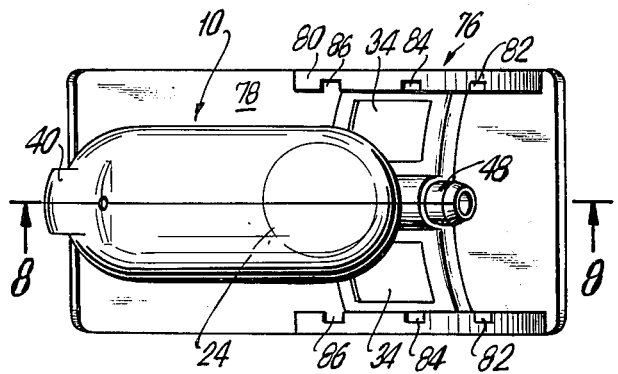
FIG. 7 is a plan view of the platform for maintaining the device in a rearwardly tilted position to reduce the inhalation effort needed to raise and maintain the ball at the top of the container.
Figure 8:
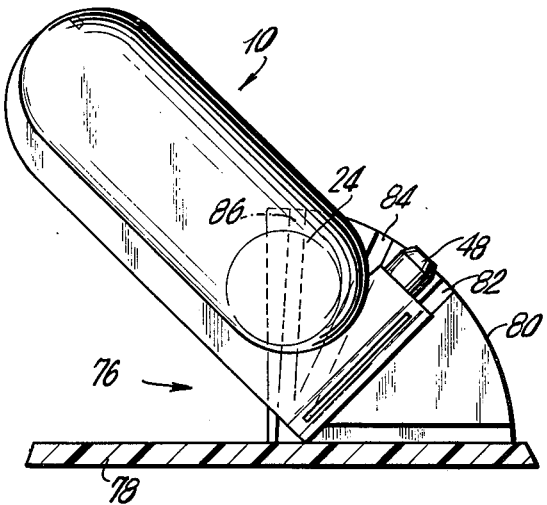
FIG. 8 is a side view with the foreground side wall removed to more clearly show the grooves into which the base of the device is slidable.
Figure 13:
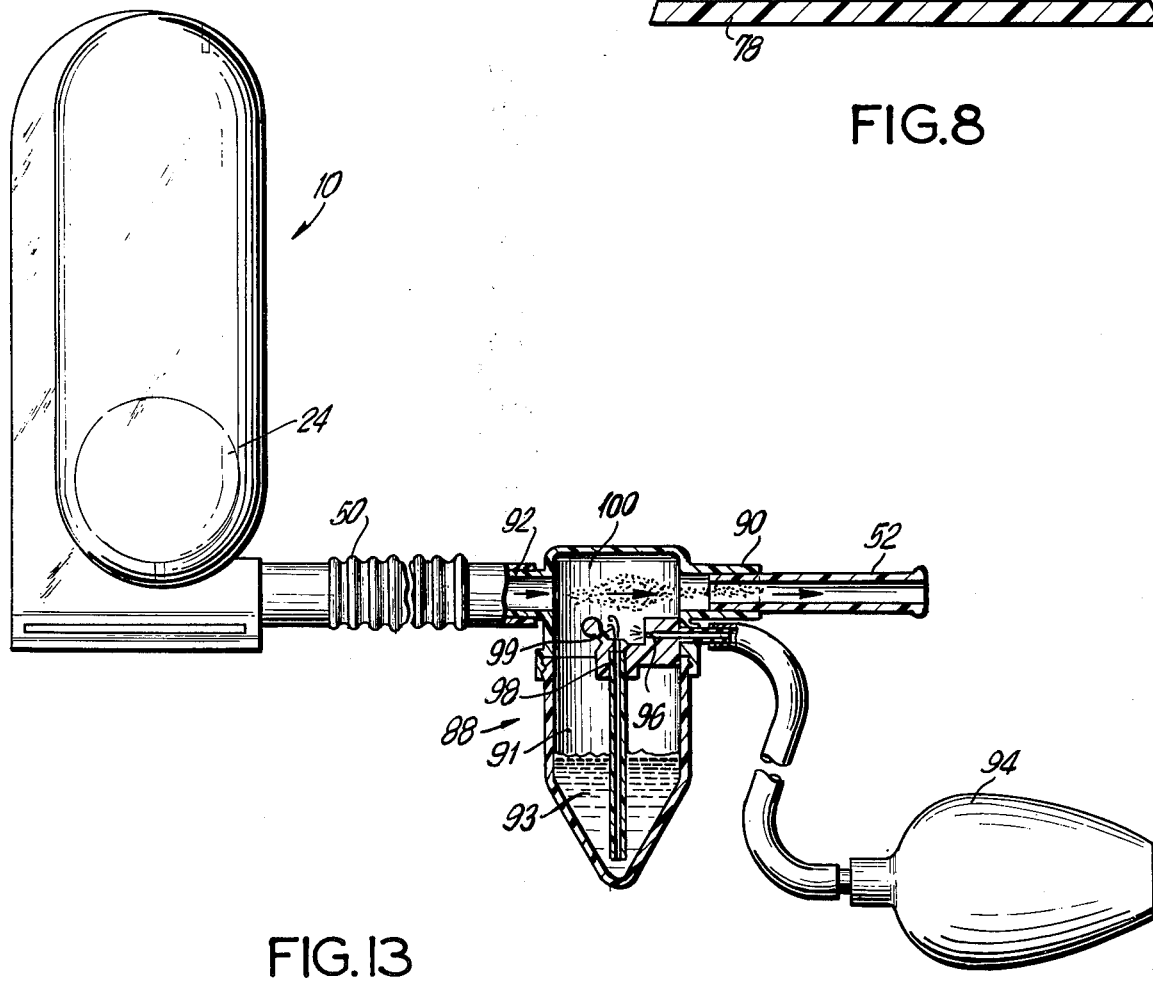
FIG. 13 is a side view, partly broken away, to show the dispenser for dispensing medicine through the flexible tubing upon inhalation with the device shown in FIGS. 1-6.

In addition, the devices 10 of the invention can be tilted to reduce the inhalation effort needed to raise and maintain the ball 24 at the top of end container 12. In the device 10 shown in FIGS. 1-6, by tilting it rearwardly, the lifting force needed to overcome the force of gravity is reduced. The greater the tilt the less the inhalation effort needed to achieve lifting and maintaining the ball at the top of the container 12. In tilting the device 10, however, it becomes more difficult to measure flow rate when the angle of tilt cannot be ascertained. To overcome this difficulty, the present invention includes, as shown in FIGS. 7 and 8, a platform 76 having a self-standing base 78 and two side walls 80. Included in each side wall are grooves 82, 83 and 84 which are set at 45°, 65° and 85° to the base 76. In use, base 14 of the container 12 is slidable into opposing grooves so that any one readily can tell the angle of the tilt.

The device 10 of FIGS. 1-6, for example, is precalibrated to provide a flow rate of 650 cubic centimeters per second at 45°; 550 cubic centimeters per second at 65°; and 250 cubic centimeters per second at 85°.

Thus, regardless of the condition of the patient, the present invention provides an incentive for a patient to use his or her lungs and chest. As that patient recovers, the angle of the tilt can be reduced until the device is vertically upright. In this way, the patient realizes his or her improvement.

Referring now to the embodiment of the invention shown in FIGS. 9–12, the reference numerals previously used are used to indicate the same or similar parts.

In this embodiment of the device 10 the opposing openings are the upper port 28 which connects chamber 22 to the air passageway 44, and a lower opening 85 which connects the lower portion of the chamber 22 to atmosphere for lifting the indicator or ball 24.

As shown, the lower opening 85 is a slot which extends through and across the front and back of the lower portion of the chamber 22 at a point which is at least partially below the ball 24. The slot 85 is rectangular in shape, and inasmuch as the container is cylindrical the slot 85 is in the shape of an arc.

As in the other illustrative embodiment of the invention described herein in detail, the ball 24 normally rests in the lower portion of the chamber 22, and the relative diameter of the article or ball 24 to the cylindrical wall 20 is such that it provides for free movement of the ball 24 within the chamber 22 while providing a minimum clearance. To support the ball in the lower portion of the chamber 22, opposing triangularly shaped ridges 86 extend inwardly from the front and back portion of the cylindrical wall 20 immediately above the slot 85. The ball 24 normally rests on the downwardly sloping surfaces 87 of the ridges 86 so that only the lowermost segment of the ball 24 extends across the upper portion of the slot 85.

In use, the patient or user places his or her mouth over the mouthpiece 52 and inhales. This concurrently causes air to be withdrawn from the air passageway 44 and chamber 22 and causes air from the surrounding atmosphere to be drawn into slot 85 beneath the ball 24. When the patient reaches the precalibrated inhalation effort the lifting forces from the incoming air will lift the ball 24 from the ridges 86 to the top of the chamber against the ridge 32. Continued inhalation of the precalibrated rate will cause the ball to remain at the top of the chamber. For each unit of time the ball remains at the top of the chamber, the patient has inhaled the precalibrated amount of air. Thus, a nurse, patient and others can tell that at least so many cubic centimeters have been inspired by timing how long the ball 24 remains suspended at the top of the container. In this illustrative example the inspirator 10 is dimensioned so that the ball 24 will rise to the top of the chamber 22 upon exerting an inhalation effort of 600 cubic centimeters per second. The chamber 22 is 4.70 inches high and has a diameter of about 1.75° inches. The ball weighs about 2.5 grams and has a diameter of about 1.700 inches, to thereby provide a total gap of about 0.075 inches between the ball and chamber wall. Each segment of the slot 85 has a length of about 1.250 inches and a height of about 0.156 inches. In this embodiment patients or users can keep the ball 24 at the top of the chamber 22 by continuing to inhale at the rate of at least 600 centimeters per second.

To increase the inhalation effort to 1000 cubic centimeters per second, only the ball size need be changed from 1.700 inches to 1.675 inches. Accordingly, this single chambered device also provides substantial flexibility and can be provided with a variety of precalibrated rates of air flow.

With respect to both illustrative embodiments of the invention shown in FIGS. 1–6 and FIGS. 9–12, moreover, the devices are constructed to give the users a clear unimpeded view of the balls 24 when they are using the devices 10.

The action of the ball in each device is readily seen because the air passageway 44 is under and up along the back of the container 12 giving the user a clear unimpeded view so that users can readily measure his or her efforts.

Further, the devices of the invention are compact and easy to handle. The illustrated devices each stand some six inches high, and each is about six inches in length and about three inches wide. Patients therefore can easily handle and operate the device. Flexible tubing 50 of some 11.0 inches has been found convenient.

As a reminder of the precalibrated flow rate required to lift the ball 24 in each of the illustrated embodiments, such information can be imprinted directly on the arm 34 of the platform or a label containing the precalibrated flow rate can be applied to the arm 34, e.g., 750 cubic centimeters per second (FIGS. 1–7) or 600 cubic centimeters per second (FIGS. 9–12).

Also, in the illustrated embodiments, the filter is made from urethane foam of about 0.57 inches in length and 0.25 inches in thickness. The illustrated filter has 10 pores per inch to present a tortuous path for the air flow to prevent loose particles from passing therethrough.

Figure 2:
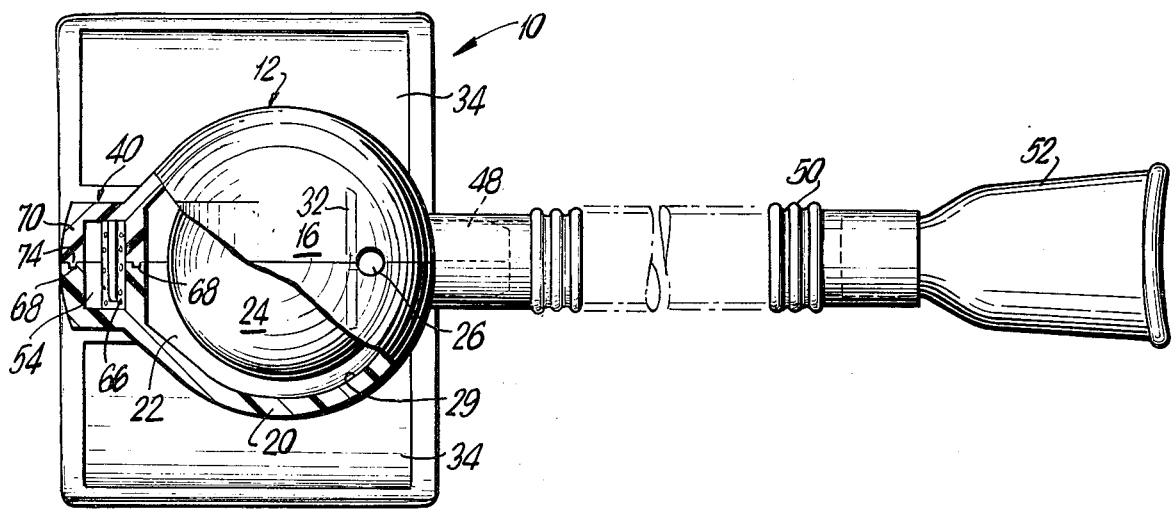
FIG. 2 is a plan view of the device illustrated in FIG. 1 with the top of the container and vertical channel away to show details of construction.
Figure 3:
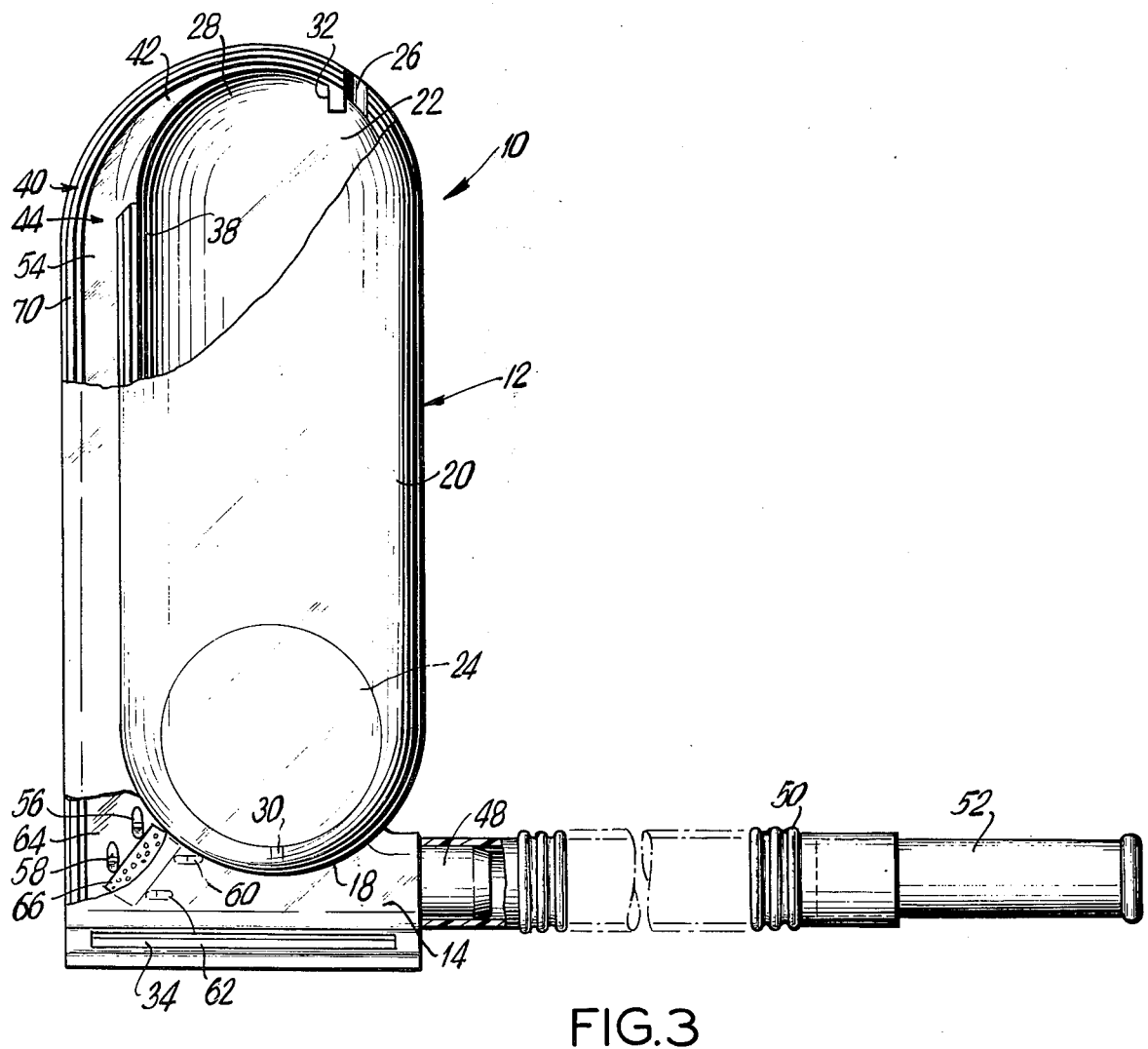
FIG. 3 is a side view of the device illustrated in FIG. 1 in which the container and vertical channel are partially broken away to show details in construction.
Figure 4:
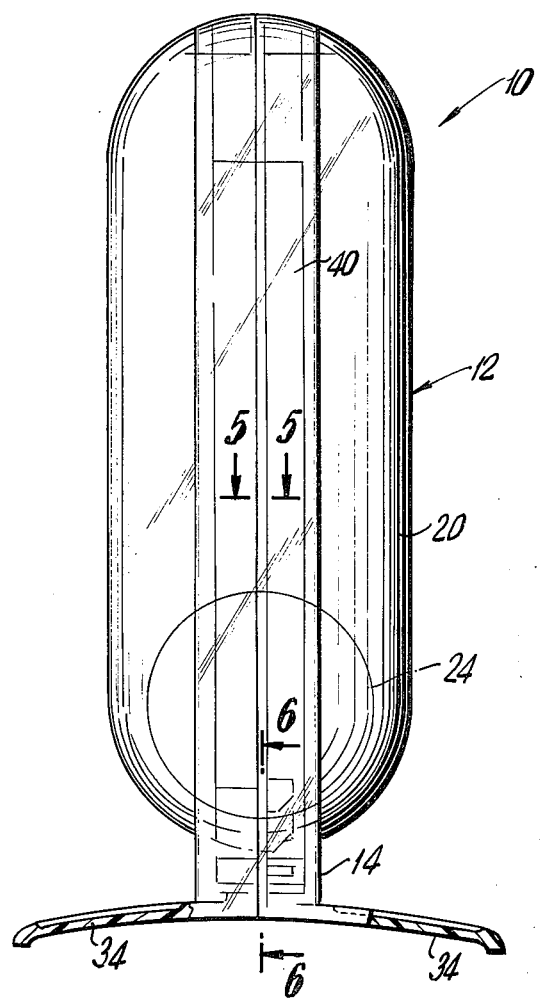
FIG. 4 is an end view looking at the back of the device illustrated in FIG. 1.
Figure 5:
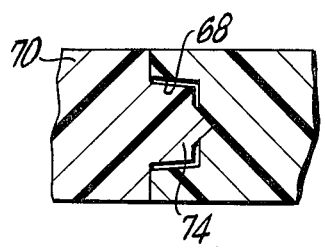
FIG. 5 is a sectional view of FIG. 4, taken along the lines 5—5, illustrating the tongue and groove construction of the mating parts.
Figure 6:
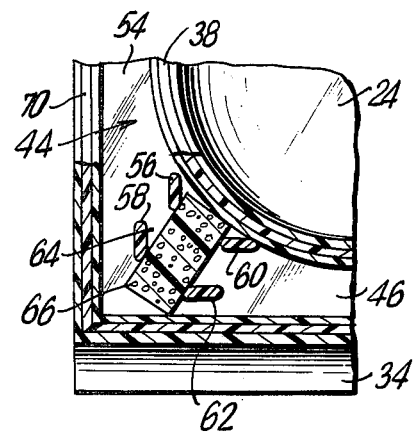
FIG. 6 is a sectional view of FIG. 4, taken along the lines 6—6, showing the filter in the air passageway which prevents loose particles from being inhalated.

With respect to the construction of the embodiments in the drawings, each inspirator 10 is formed in a two part conventional injection mold. Each part is a vertical section of the inspirator, which, as illustrated in FIG. 2, is one-half of the assembled inspirator taken along a center line which cuts across the channel 40 and container 12. Also, as illustrated in FIGS. 2 and 5, the face of the lower or right hand section is formed with grooves 68 in the container inner wall 38 and channel outer wall 70. Correspondingly, the upper or left hand section is formed with tongues 74 in the container inner wall 38 and the channel outer wall 70 which slidably fit into the grooves 68.

In assembling the illustrated inspirators, the filter 66 for each device 10 is inserted in the slot 64, a ball 24 is placed in one section of the container 12 and the molded sections are brought together so as to cause the tongues 74 to fit into the grooves 68. With the inspirator 10 assembled, the sections are ultrasonically welded together to form a single integral device 10. In so doing, the need for glue, the deleterious vapors of which remain long after use, is obviated.

The devices 10 of the invention are preferably formed from plastics which are inert and stable in the formed device 10 and which lend themselves to processing by plastic forming techniques, and will, when formed, provide the break resistant, see-through self-supporting device described and claimed herein. In the preferred embodiment the see-through device is formed by injection molding polystyrene. Other materials and plastics which provide the desired see-through properties also can be used, including styrene-acrylonitrile copolymers, rigid polyvinylchloride polymers and poly carbonate polymers.

Figure 9:
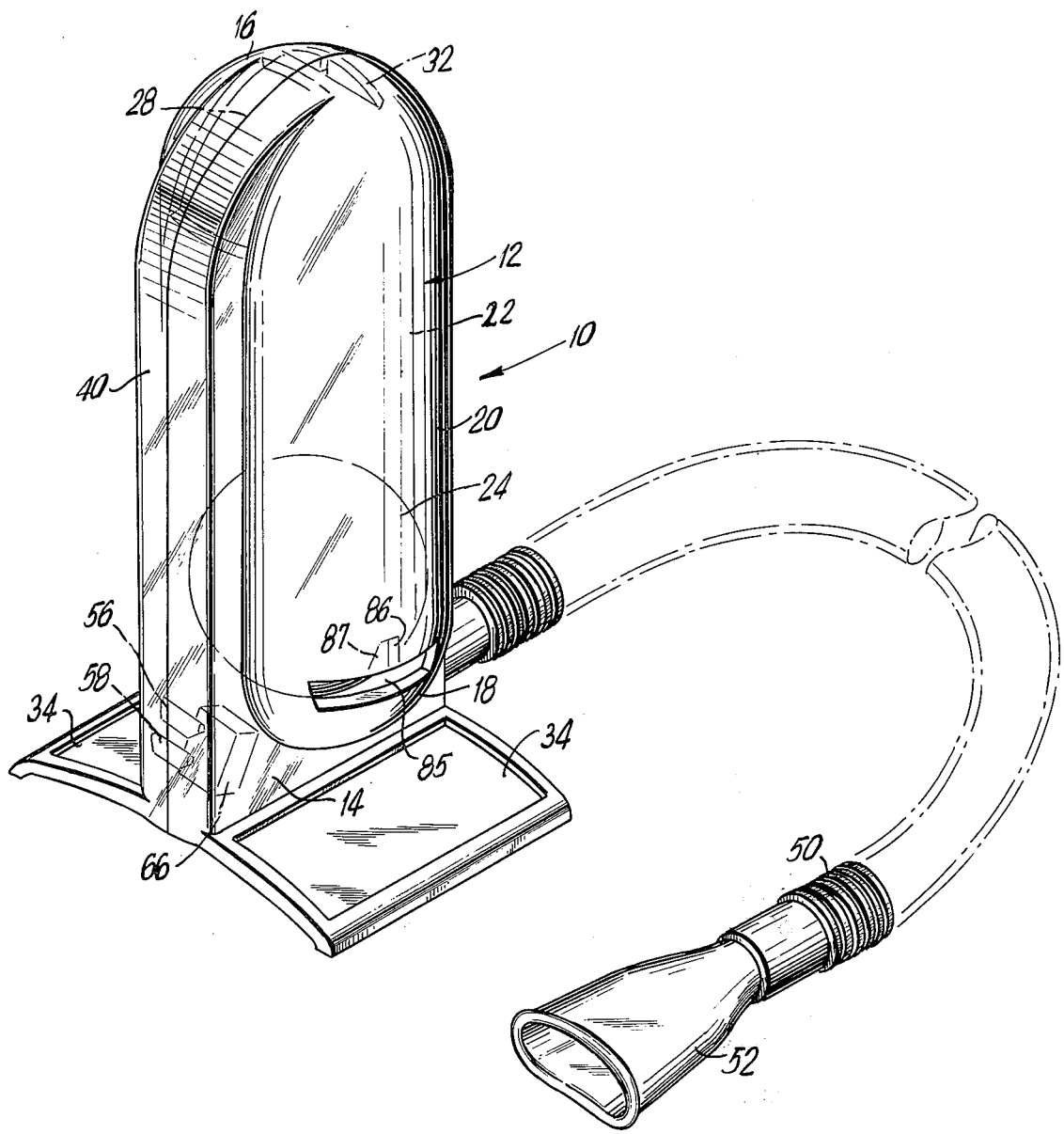
FIG. 9 is a perspective view of another inhalation device constructed in accordance with the present invention, wherein opposing openings are provided in the upper and lower portions of the container.
Figure 14:
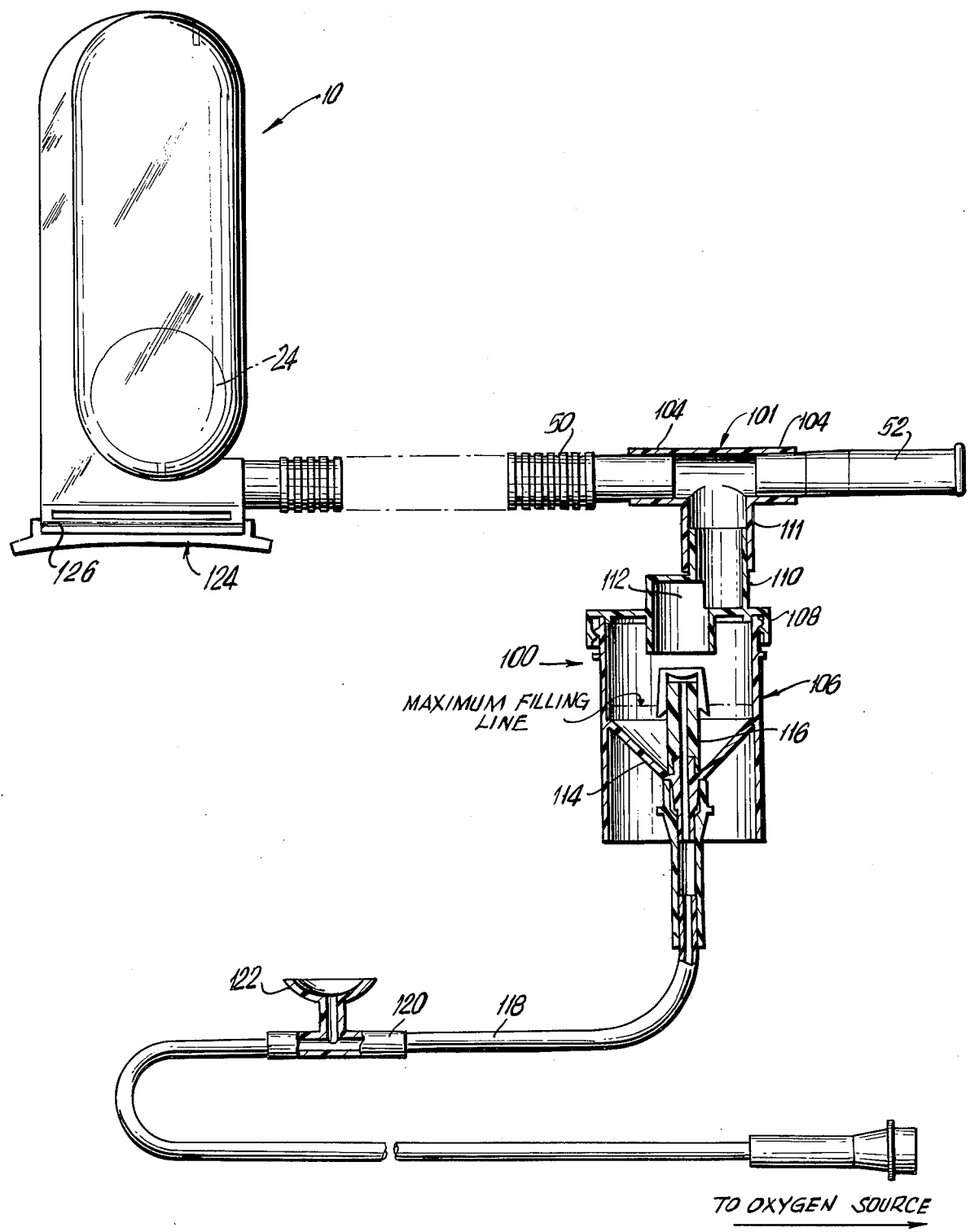
FIG. 14 is a side view, partly broken away, to show the dispenser for dispensing medicine through the flexible tubing upon inhalation with the device shown in FIGS. 9-12.

As shown in FIGS. 9 and 14, the present invention also can employ medicinal dispensers 88 and 101 connected to the devices 10 between the tubing 50 and the mouthpiece 52. Upon inhalation the patient will inspire the medicine as he or she uses his or her lungs and musculature. Accordingly, the doctor nurse or others will known that the patient is inhaling the medication because the patient's efforts should cause the ball 24 in the chamber 22 to rise. The illustrated medicinal dispensers 88 and 101 can be used to dispense bronchial dilators, water vapor, anti-inflammatory agents and asthmatic and other medicines.

In FIG. 9 the dispenser 88 is directly connected at one end 90 to the mouthpiece 52 and at the other end 92 to the tubing 50 of the device shown in FIGS. 1–7. As shown, a reservoir 91 is filled with medication 93 usually around 5 cubic centimeters. While inhaling, the patient squeezes the bulb 94. Air from the bulb is forced through the nozzle 96 and across the tip of the tube 98. This rapidly-forced air creates an upward venturi suction in the tube 98, thus lifting up medication from the reservoir 91. As medication squirts out the tube 98, the rapidly-forced air breaks up the liquid into an aerosol mist. The aerosol is further atomized by the diffuser 99 into smaller particles. Atomized medication is now in the upper mist chamber 100. Inhaled patient air rushes across the mist chamber 100, thus carrying the atomized medication into the respiratory system of the patient. Large, unwanted particles fall back down into the reservoir 91. Only the desired small 0.5 micron to 6 micron particles are inhaled to reach deep into the lungs. The amount of medication delivered is controlled by viewing through the reservoir 91.

In FIG. 14, a hollow T-shaped manifold 102 is used to connect the medicinal dispenser 101 to the devices 10 shown in FIGS. 9–12. The ends of the hollow horizontal segment 104 of the T-shaped manifold 102 slidably fit over the ends of the flexible tube 50 and the reduced portion of the mouthpiece 52.

The dispenser 101 includes a see-through, hollow cylindrical tube 106 having a cap 108 threaded thereon. The cap 108 includes an upwardly extending offset outlet tube 110 which slidably fits into the depending vertical, hollow leg 111 of the T-shaped manifold 102, and which forms with the cap 108 a circuitous passageway between the interior of the hollow cylindrical tube 106 and the hollow T-shaped manifold 102.

Within the cylindrical tube 106 is a funnel 114 which is secured to the central portion thereof. As shown, the funnel 114 is adapted to hold the medicine which is to be inhalated. Extending through the funnel 114 is a capped atomizing conduit 116. Slidably fitted over the lower end of the conduit 116 below the funnel is a flexible tube 118 connected at its other end to an oxygen panel generally disposed next to a patient's bed.

Connected into the flexible tubing 118 downstream of the dispenser 101 is a hollow thumb control manifold 120, having an opening 122, which is normally open to atmosphere. To close the manifold 120, and thereby allow oxygen to be fed to the dispenser 101 one simply has to place his or her thumb over the manifold opening 122.

To use the dispenser 101 the cap 108 is removed and the funnel 114 and adjacent portion of the tube 106 are filled with medicine up to the "max fill line". The cap 108 is then threaded onto the tubing 106 and the offset tube 110 is inserted into the depending leg 111 of the T-shaped manifold 102.

The patient now can inhale the medicine by simply closing the thumb opening 122 and inhaling through the mouthpiece. This causes oxygen impinging upon the cap of the conduit 116 to flow downwardly into the medicine and then upwardly with the medicine through the pasageway 112, the T manifold 102, the mouthpiece 58 and into the lungs of the user.

With the devices 10 of the invention one can be assured that the patient is inhalating the atomized medicine becuase a proper inhalation effort will cause the flow indicator 24 to rise.

To insure stabilization of the device 10 when it is being used with the medicinal dispensers 88 and 100, and as shown in FIG. 15, a platform 124 can be used. As illustrated, the platform 124 has a breadth which is substantially greater than the breadth of the platform of the device 10, and includes a channel 126 into which the platform slidably fits.

The invention in its broader aspect is not limited to the specific described embodiments and departures may be made therefrom within the scope of the accompanying claims without departing from the principals of the invention and without sacrificing its chief advantages.

What is claimed is:

1. A self-supporting incentive inhalation device for inducing respiratory exercises comprising:

a container, having a front and back portion, a top wall and a bottom wall and an intermediate see-through wall forming a chamber within said container which extends between said top and bottom walls, a light-weight article in said chamber normally at the bottom thereof, but which, upon inhalation by the user at a precalibrated flow rate, will rise towards the top thereof, an opening extending through the upper portion of said container and into said chamber wherein air flows through said opening from the upper portion of said chamber upon inhalation, an opening extending through the lower portion of said container and into said chamber to open said chamber to atmosphere, and wherein air flows from atmosphere through said opening into the lower portion of said chamber for lifting said article upon inhalation, an inhalation passageway integral with said device wherein said passageway extends from the front and bottom of said container and up along the back of said container and being formed by the surface of said walls adjacent said passageway and a channel integral therewith, and, where at its upper end, said passageway is connected to said upper opening, and means connected to said passageway at the front and bottom of said container to allow a person to withdraw air from said chamber to cause atmospheric air to flow into the chamber through said lower opening, through said chamber and into said upper opening and passageway, which causes said article therein to rise to and be maintained at the top of said chamber when the user reaches and maintains an inhalation effort that is at least at the precalibrated flow rate, said passageway and last said means leaving a clear view of said chamber within said container so that said article in said chamber easily can be seen and followed by the user.

2. The inhalation device according to claim 1, wherein said lower opening extends through and across said container at a point at least partially below said article, and said upper opening is restricted relative to said lower opening.

3. The inhalation device according to claim 2, wherein said container includes an inner wall which forms said chamber, and wherein means extend from said inner wall into said chamber in the lower portion thereof to support said article so that said lower opening is always at a point at least partially therebelow.

4. The inhalation device according to claim 2, wherein means are provided in said chamber which prevents said article therein from closing said upper opening.

5. The inhalation device according to claim 1, wherein said container is mounted on a base upon which the device stands in an upright position.

6. The inhalation device according to claim 1, wherein said article is a light-weight ball.

7. The inhalation device of claim 1, in which said precalibrated flow rate is from about 600 to about 1000 centimeters per second.

8. The inhalation device of claim 1, in which the device is made of polystyrene and is formed from a plurality of pieces ultrasonically welded together into a single, integral unit.

9. The inhalation device of claim 1, in which said device includes a platform into which said container is slidable at predetermined acute angles to reduce the flow rate necessary to cause said article to rise and be maintained at the top of said container.

10. The inhalation device of claim 1, in which a medicinal dispenser is connected between said outlet and said tubing for dispensing medicine upon inhalation.

11. The inhalation device of claims 1, which a medicinal dispenser is connected to said outlet for dispensing atomized medicine upon inhalation, wherein said dispenser includes:
   a container for holding medicine to be inhaled,
   gas conveying means adapted to be connected to a source of gas and positioned within said container for atomizing the medicine therewithin, and
   a passageway connected and open to said container and said outlet for conveying atomized medicine from said container and into said outlet upon inhalation by a person.

12. The inhalation device of claim 1 in which a medicinal dispenser is connected to said outlet for dispensing medicine upon inhalation, wherein said dispenser includes:
   a container having a funnel therewithin for holding medicine to be atomized,
   an atomizing conduit extending through said funnel and adapted to atomize medicine hold by said funnel,
   flexible tubing adapted to be connected to said atomizing conduit and to a source of oxygen for providing oxygen to said atomizing conduit for atomization of the medicine,
   means operatively connected to said flexible tubing for controlling the flow of oxygen therethrough to thereby provide to said atomizing conduit only when the medicine is to be atomized, and
   a circuitous passageway connected and open to said container and said outlet for conveying atomized medicine from said container into said outlet upon inhalation by a person.

13. The inhalation of claim 12 in which a removable platform is adapted to be attached to the bottom of the device when the medicinal dispenser is to be used to provide increased stability.

14. A self-supporting incentive inhalation device for inducing respiratory exercise, comprising:
   a container having a front and back portion, a top wall and a bottom wall, and a vertical see-through cylindrical wall therebetween forming a chamber which extends between said top and bottom wall,
   a light-weight ball in said chamber normally in the lower portion thereof which has a clearance with respect to said cylindrical wall to allow said ball to rise and be maintained at the top of said container upon inhalation at a precalibrated flow rate,
   a slot extending through and across the lower portion of said container and into said chamber to open said chamber to atmosphere, wherein air flows from atmosphere through said opening into the lower portion of said chamber for lifting said ball upon inhalation,
   an opening extending through the upper portion of said container and into said chamber, wherein air flows through said opening from the upper portion of said chamber upon inhalation, and wherein said opening is restricted relative to said slot,
   means extending from said cylindrical wall of said container into said chamber immediately above said slot to support the ball so that only the lowermost segment thereof can extend across the upper portion of said slot,
   means extending from said topwall into said chamber to prevent said ball from closing said upper opening and disrupting air flow therethrough,
   a base integral with the bottom of said container which extends outwardly to make said device self-supporting in an upright vertical position,
   an inhalation passageway integral with said device wherein said passageway extends from the front and bottom of said container through said base and up along the back of said container, said passageway extending along the back of said container and being formed by the outer surface of said walls adjacent said passageway, and a channel integral therewith, and, where at its upper end, said passageway is connected to said upper opening, and
   flexible tubing connected at one end to said passageway at the front of and below said container, and a mouthpiece connected at the other end of said flexible tubing to allow a person by inhalation to withdraw air from said chamber to thereby effect air flow into said chamber through said lower slot and air flow from said chamber through said upper opening which creates a lifting stream of air flow that causes said ball to rise to the top of the chamber and remain there as long as the inhalation effort is maintained at the predetermined flow rate,
   said passageway, tubing and mouthpiece leaving a clear front view of the see-through container cylinder so that said light-weight article in said chamber can be easily seen and followed by the user.

15. A self-supporting incentive inhalation device for inducing a person to expand and use his or her lungs, comprising:
   a transparent container having a hemispherically shaped top and bottom walls and cylindrical wall therebetween which forms a chamber in said container which extends from said bottom to said top walls,
   a ball in said chamber having a minimum clearance with said cylindrical wall which normally rests in the bottom portion thereof but which upon inhalation at a precalibrated flow rate selected from the range of about 600 to 1000 cubic centimeters per second will cause said ball to rise and be maintained at said container top, a slot extending through and across the lower portion of said container and into said chamber to open said chamber to atmosphere, wherein air flows from atmosphere through said opening into the lower portion of said chamber for lifting said ball upon inhalation, an opening extending through the upper portion of said container and into said chamber, wherein air flows through said opening from the upper portion of said chamber upon inhalation, and wherein said opening is restricted relative to said slot, means extending from said cylindrical wall of said container into said chamber immediately above said slot to support the ball so that only the lowermost segment thereof can extend across the upper portion of said slot.

means extending into said chamber from said top wall to prevent said ball from closing said upper opening and disrupting air flow therethrough, said a base on which said container is positioned and from which said base laterally extends so that the device stands by itself in the vertical upright position, a closed vertical channel extending upwardly from said base along the back of said container to and over said back port, an inhalation passageway having an outlet below said container and in front of said device and extending horizontally through said base under said container vertically upward through said channel where it is connected to said upper opening, and flexible tubing connected to one end thereof to said passageway outlet and at the other end thereof to a mouthpiece to allow the user by inhalation to withdraw air from said chamber which at the selected flow rate will cause said ball to rise to and be maintained at said container top for as long as said flow rate is maintained.

* * * * *

UNITED STATES PATENT AND TRADEMARK OFFICE
CERTIFICATE OF CORRECTION

PATENT NO. : 4,114,608
DATED : September 19, 1978
INVENTOR(S) : Ronald D. Russo

It is certified that error appears in the above-identified patent and that said Letters Patent are hereby corrected as shown below:

Col. 3, line 13, "provide" should read --provided--.

Col. 7, line 51, After "1.75" delete --°--.

Col. 8, line 65, After "doctor" a comma --,-- should be inserted.

line 66, Correct "known" to read --know--.

Col. 9, line 65, After "T" insert a dash -- - --.

Col. 11, line 14, Before "centimeters" insert --cubic--.

line 28, Correct "claims" to read --claim--.

line 47, Correct "hold" to read --held--.

UNITED STATES PATENT AND TRADEMARK OFFICE
CERTIFICATE OF CORRECTION

PATENT NO. : 4,114,608
DATED : September 19, 1978
INVENTOR(S) : Ronald D. Russo

It is certified that error appears in the above—identified patent and that said Letters Patent are hereby corrected as shown below:

Col. 13, line 16, After "slot" delete the period "." and insert a comma --,--.

line 19, Delete "said" and insert --and--.

Signed and Sealed this

Twenty-first Day of August 1979

[SEAL]

Attest:

LUTRELLE F. PARKER

Attesting Officer     Acting Commissioner of Patents and Trademarks